(12) United States Patent
Dunn

(10) Patent No.: US 8,251,915 B2
(45) Date of Patent: Aug. 28, 2012

(54) DERMAL PUNCH DEVICE

(75) Inventor: Raymond Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 584 days.

(21) Appl. No.: 12/383,368

(22) Filed: Mar. 23, 2009

(65) Prior Publication Data
US 2009/0264795 A1 Oct. 22, 2009

Related U.S. Application Data

(62) Division of application No. 10/943,051, filed on Sep. 16, 2004, now abandoned.

(60) Provisional application No. 60/503,351, filed on Sep. 16, 2003.

(51) Int. Cl.
*A61B 10/00* (2006.01)
*A61B 17/14* (2006.01)
*A61B 17/32* (2006.01)

(52) U.S. Cl. .................. 600/564; 600/567; 606/184

(58) Field of Classification Search .......... 600/562–568; 606/167, 170, 171, 184
See application file for complete search history.

(56) References Cited

U.S. PATENT DOCUMENTS

| | | | |
|---|---|---|---|
| 3,171,457 A * | 3/1965 | Brown | 83/849 |
| 3,990,451 A | 11/1976 | Gibbs | |
| 4,557,172 A * | 12/1985 | Yoneda | 83/848 |
| 4,682,606 A * | 7/1987 | DeCaprio | 600/567 |
| 5,183,053 A | 2/1993 | Yeh et al. | |
| 5,209,755 A | 5/1993 | Abrahan et al. | |
| 5,507,765 A | 4/1996 | Mott | |
| 5,570,700 A | 11/1996 | Vogeler | |
| 5,693,064 A | 12/1997 | Arnold | |
| 5,788,651 A | 8/1998 | Weilandt | |
| 5,961,529 A | 10/1999 | Arnold | |
| 6,027,458 A | 2/2000 | Janssens | |
| 6,027,512 A | 2/2000 | Bridges | |
| 6,080,176 A | 6/2000 | Young | |
| 6,277,083 B1 * | 8/2001 | Eggers et al. | 600/564 |
| 6,770,070 B1 * | 8/2004 | Balbierz | 606/41 |
| 2002/0052619 A1 | 5/2002 | Transue | |
| 2003/0097144 A1 | 5/2003 | Lee | |
| 2004/0167430 A1 | 8/2004 | Roshdieh et al. | |

FOREIGN PATENT DOCUMENTS

WO WO 00/24323 5/2000

* cited by examiner

*Primary Examiner* — Max Hindenburg
*Assistant Examiner* — Jonathan M Foreman
(74) *Attorney, Agent, or Firm* — Weingarten, Schurgin, Gagnebin & Lebovici LLP

(57) ABSTRACT

A dermal punch for extracting skin or tissue samples. The dermal punch has a blade having a pair of walls. Each wall is convex and opens towards each other. The walls are connected to each other at a pair of mating edges. Each wall has a cutting edge. In a preferred embodiment, the ratio of the minor axis to the major axis of the opening created by the walls is between 1 to 3 and 1 to 4, wherein the major axis extends through the mating edges. The cutting edge is formed of a plurality of teeth and the teeth have a sawtooth shape. The cutting edge has a projecting edge for each wall, and the projecting edge is concave. The cutting length is greater than twice the length of the projecting edge.

26 Claims, 19 Drawing Sheets

RESULTANT WOUND

FINAL "SCAR"

DERMAL PUNCH DEVICE

CROSS REFERENCES TO RELATED APPLICATIONS

The present application claims the benefit and is a divisional of U.S. application Ser. No. 10/943,051 filed Sep. 16, 2004 and of U.S. Provisional Application No. 60/503,351, filed Sep. 16, 2003. The entire contents of the above applications are incorporated herein by reference.

BACKGROUND OF THE INVENTION

Thousands of people are tested annually for melanoma, basal cell, squamous cell, and carcinogens, other abnormal skin growths ("moles") and cancers, as well as bacterial or fungal skin infections. One of the most common tests of a skin lesion for diagnostic purposes is a dermal punch biopsy. This procedure entails the insertion of an instrument with a circular blade into the patient's skin and then subsequently rotating the instrument to cut out and remove the skin patch of interest. This provides tissue for microscopic analysis by a pathologist to obtain the correct diagnosis. This technique is nearly 100% effective, and accurate and is consequently widely used.

Although effective, this traditional punch biopsy usually leaves the wound open resulting in delayed healing and unsightly scars. The wound can result in scars that resemble "pock-marks" or "divets." If the skin excision is large, the resultant wound can be closed by stitching but because of the circular shape of the wound, it can leave an ~even skin edge.

SUMMARY OF THE INVENTION

The preferred embodiments of the invention relate to a dermal punch and a method of using it to extract tissue samples. In a preferred embodiment, the dermal punch has a handle portion and a blade having a pair of walls. The walls can have an external convex surface that are connected to each other at a pair of mating edges. Each wall has a distal cutting edge surrounding a cavity that defines the area of removal.

In a preferred embodiment, the ratio of the minor axis to the major axis of the opening or cavity defined by the walls is at least 1 to 2 and preferably between 1 to 3 and 1 to 4, wherein the major axis extends through the mating edges. As the size and shape of the lesion to be removed can vary, a variety of dermal punches of selected ratios and removal areas can be available depending on the anatomy and orientation of the specific site requiring biopsy, such as in a kit. The kit can include a single handle and a plurality of distal punch elements that can be mounted and detached from the handle as needed or individually mounted punches.

In a preferred embodiment, the cutting edge is formed of a plurality of teeth. The teeth can have a sawtooth shape, for example. In one embodiment, the distal tip of the teeth defines a projecting edge for each wall, and the projecting edge is convex or concave. The cutting length is greater than twice the length of the projecting edge for each wall.

In a preferred method, the cutting edge is positioned relative to a selected patch of skin. The skin is punctured by the cutting edge on the dermal punch by pushing the dermal punch into the skin. The dermal punch is removed from the body by pulling the dermal punch in a motion perpendicular to the skin. The dermal punch can also be tilted such that a portion of a cutting edge cuts laterally through the fat underlying the portion of skin being removed to aid in removal.

In one method, the positioning includes placing the apex of each projecting edge in contact with the skin, with the selected patch of skin to be excised interposed between each apex. The distal end is then manually inserted through the skin and rotated or rocked to sever the sample from the underlying layer. The wound in the skin is then closed. One method of closing is to use a medical glue or adhesive. Another method of closing uses a surgical staple. Another method uses surgical tape closure to pull the edges together.

In a preferred embodiment, the distal ends of the walls are tapered in towards the center axis of the handle. In another, the spacing between the walls or the angle of the taper is adjustable.

In one embodiment, the dermal punch includes a mechanism for closing the wound. The mechanism can be a device for applying a medical glue or adhesive. In another embodiment, the mechanism is a device for applying at least one staple or a suture.

Although effective, a traditional punch biopsy usually leaves the wound open, resulting in delayed healing and unsightly scars. The open wound results in scars that resemble "pock-marks." If the skin excision is large, the resultant wound can be closed by stitching. The dermal punch according to the invention forms a wound with clean edges. A fusiform or spindle shape of an embodiment of the dermal punch with a distal taper can facilitate healing of the wound with minimal or no pocking on the skin.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
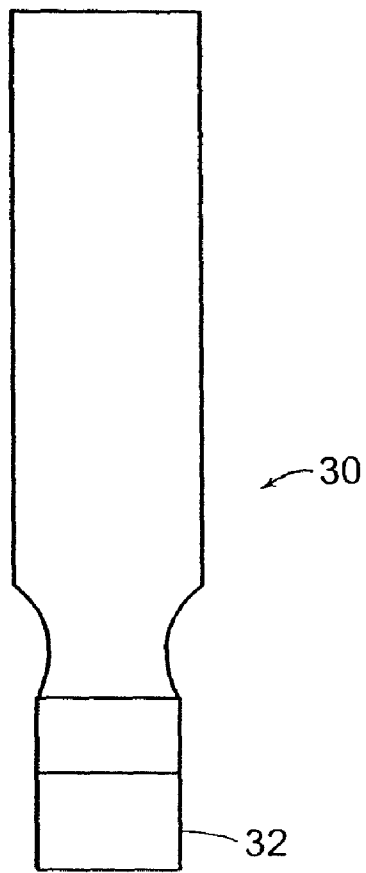
FIG. 1A is a perspective view of a dermal punch or biopsy punch of the prior art.

Referring to the drawings in detail, where like numerals indicate like elements, a dermal punch is illustrated in accordance with a preferred embodiment of the present invention designated generally as 20.

Figure 1B:
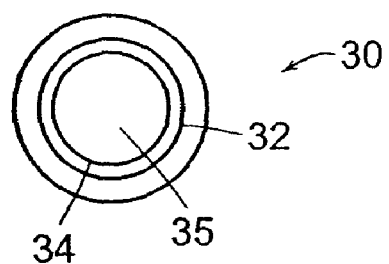
FIG. 1B is a bottom view of the dermal punch of FIG. 1A showing the cutting edge of the prior art.

FIGS. 1A and 1B show a perspective view and a bottom view respectively of a prior art dermal punch 30. The dermal punch 30 has a circular end 32 with a blade edge 34. The blade edge 34 defines a circular opening 35 which corresponds to the area of removal and is placed in engagement with a portion of the patient's skin 36 and rotated to excise the skin sample 38 of interest, as best seen in FIG. 2A.

Typically, the skin sample 38 is connected to the body by adhesion to the underlying fat layer. The skin patch 38 is removed from the body by a pair of forceps or a sharp object such as a needle.

Figure 2A:
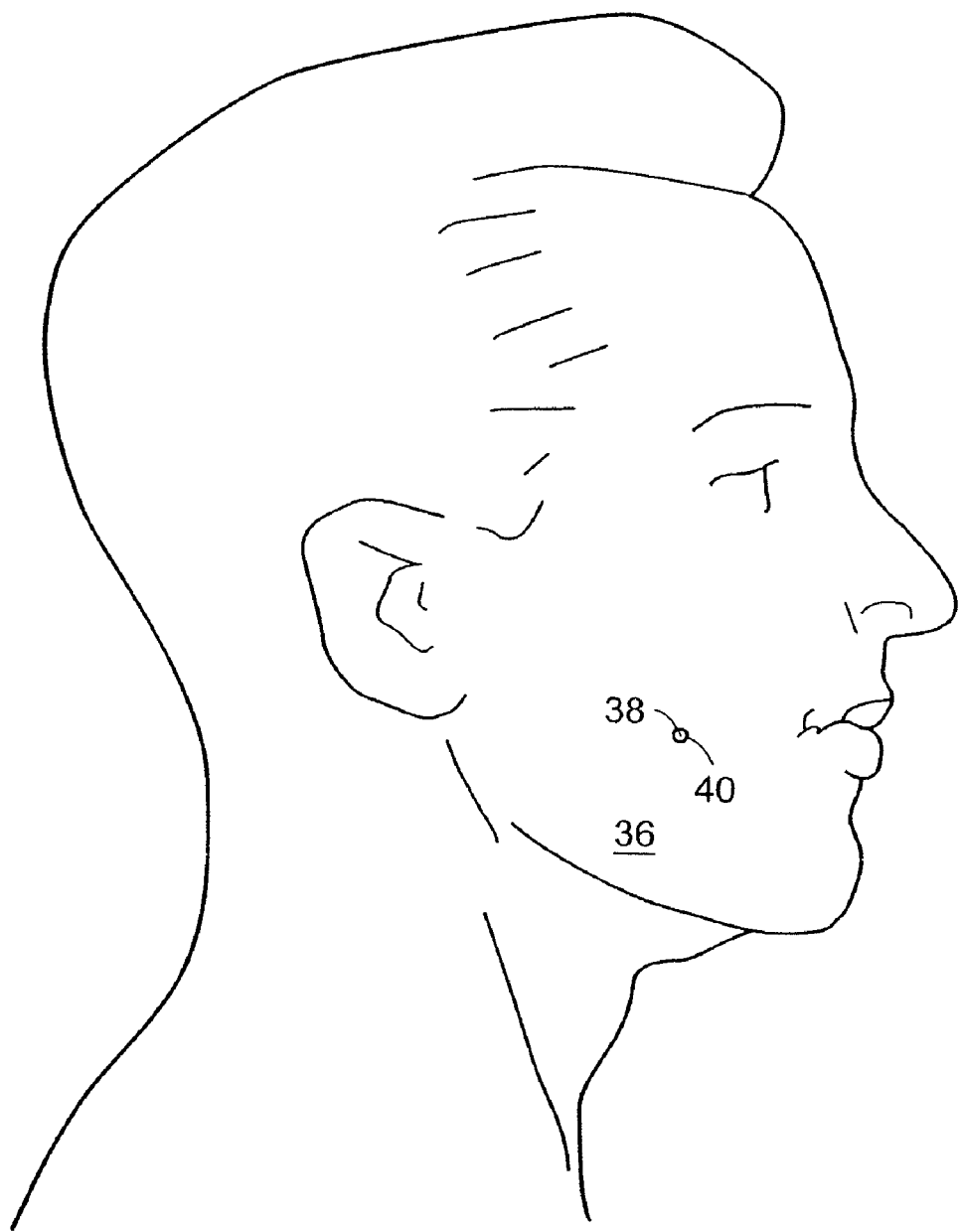
FIG. 2A is a view of an example of a wound resulting from the use of a prior art punch.
Figure 2B:
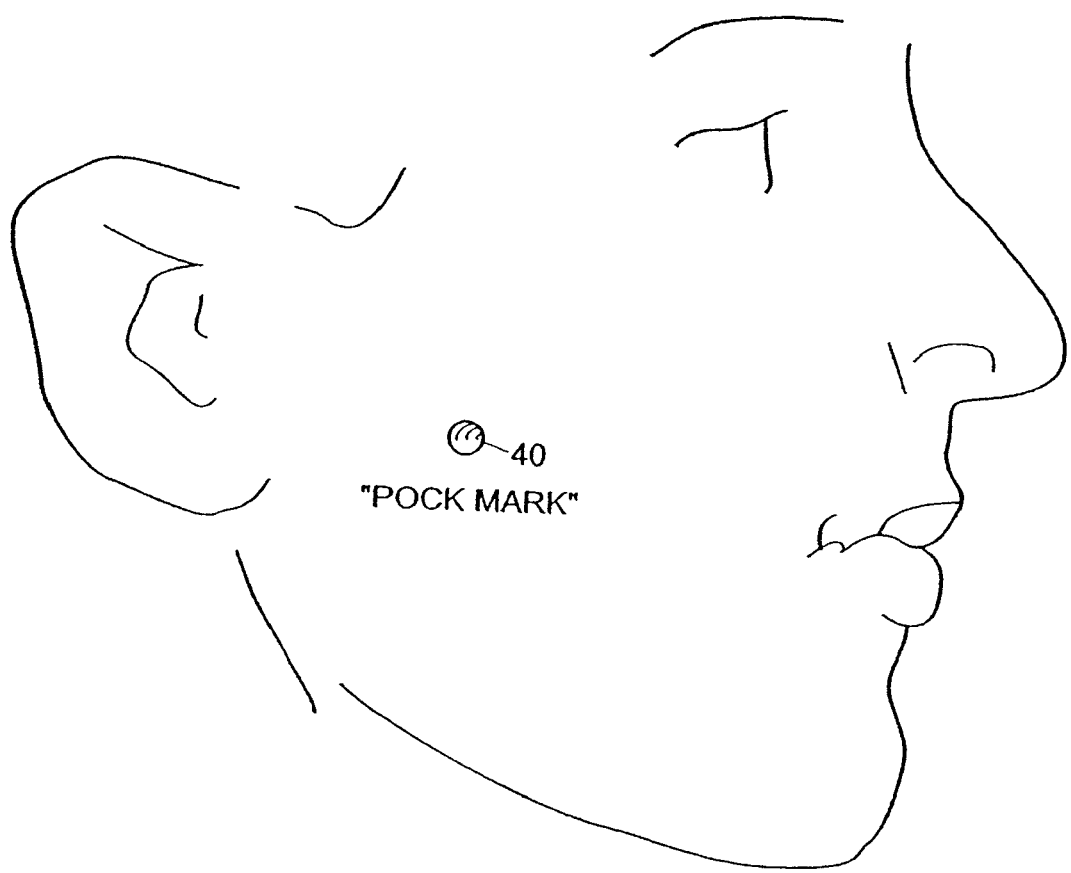
FIG. 2B is an enlarged view of an example of the resulting wound with the prior art punch.
Figure 2C:
FIG. 2C is a side sectional view of skin revealing the depression created by a "divet" of healing from a traditional punch device.
Figure 2D:
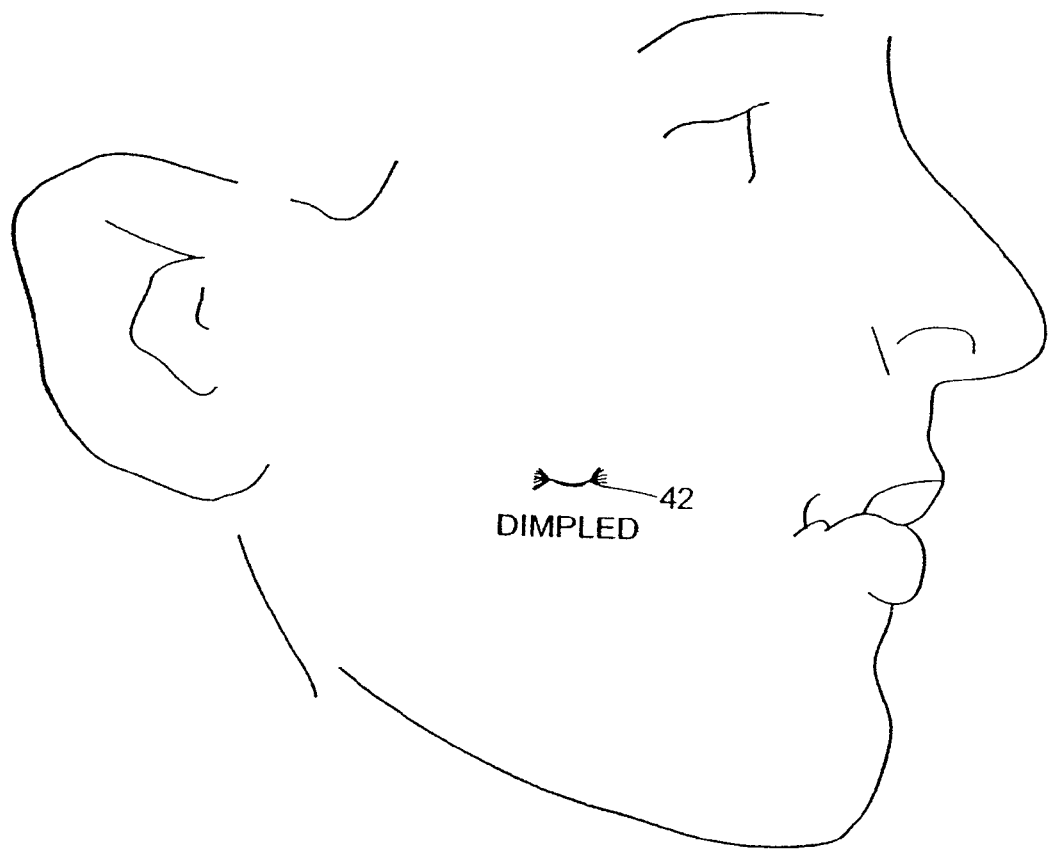
FIG. 2D is a view of an example of the resulting scar with the prior art punch.

FIG. 2A shows a wound 40 created by the removal of the skin patch 38 by the prior art dermal punch 30. The circular wound 40 is either left to heal on its own or is closed using sutures. Regardless, the wound 40 results in a deformity, such as a scar, for example, that resembles a pock-mark 40 as shown in FIGS. 2B and 2C if the wound is left to heal on its own. If sutures are used, the dimple resembles a noticeable "dog ear" scar 42, as seen in FIG. 2D.

Figure 3:
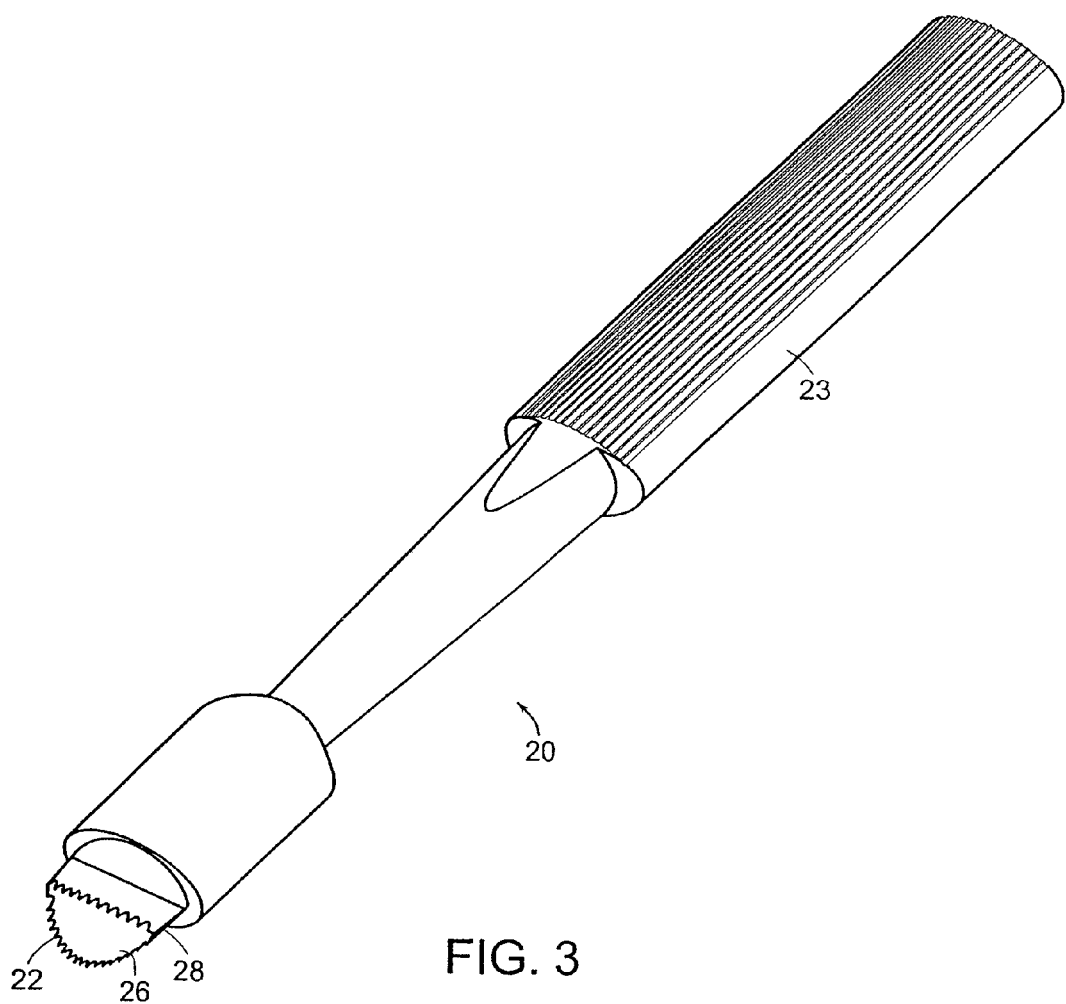
FIG. 3 is a prospective view of a dermal punch according to a preferred embodiment of the present invention.
Figure 4A:
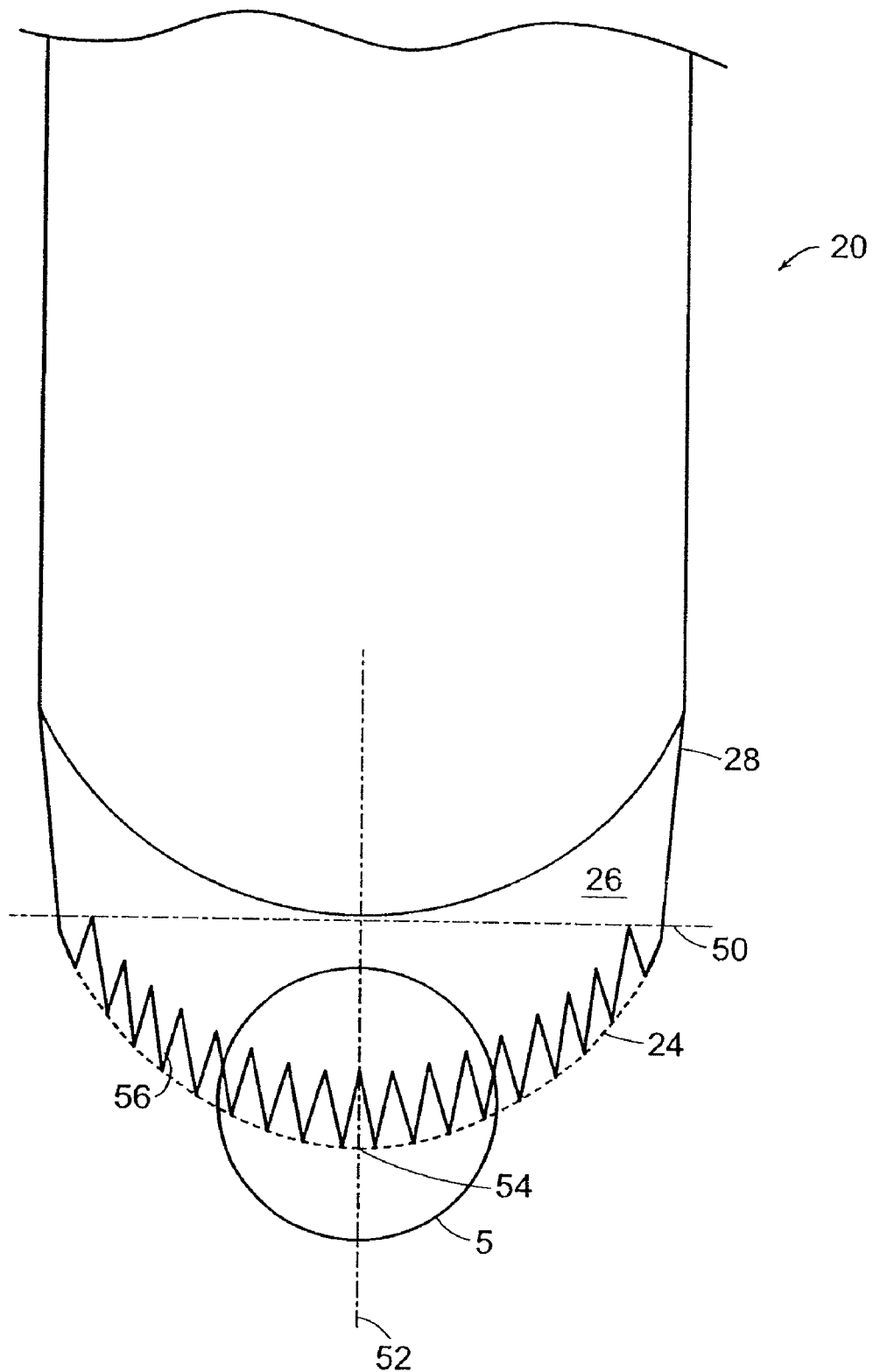
FIG. 4A is a side view of a dermal punch according to a preferred embodiment of the present invention.
Figure 4B:
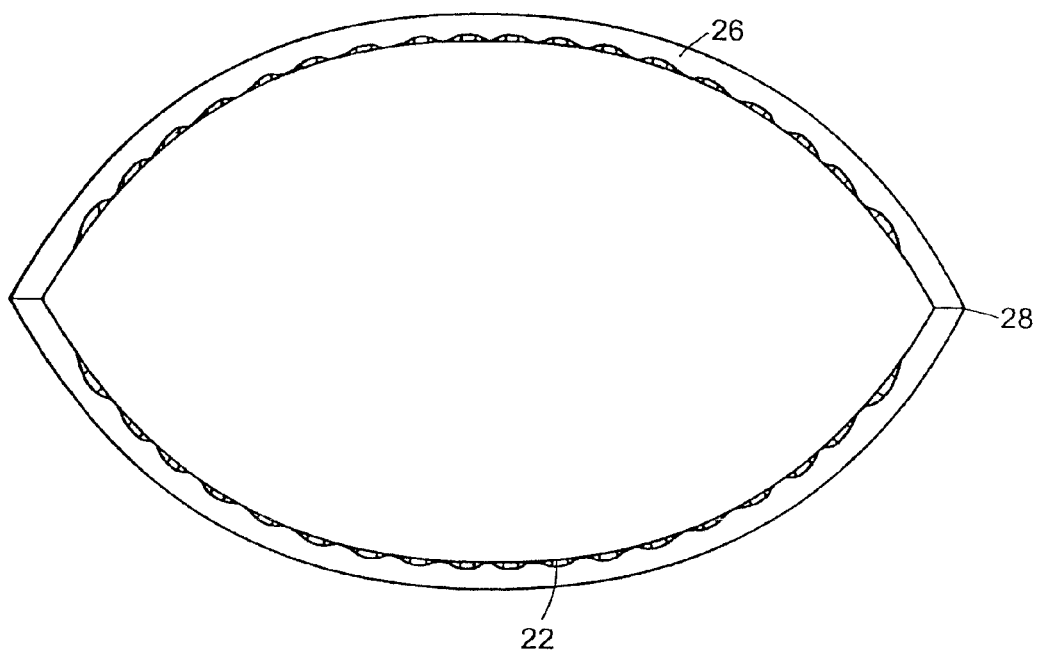
FIG. 4B is a bottom view of the dermal punch of FIG. 3.

The dermal punch 20 according to a preferred embodiment of the invention is shown in FIGS. 3, 4A, and 4B. The dermal punch 20 has a cutting or blade edge 22 that is not all located in a single plane. The cutting edge 22 is formed by a plurality of teeth that can be located at various vertical heights. The dermal punch 20 has a handle 23, as best seen in FIG. 3.

As seen in FIG. 4A, the dermal punch 20 has a projecting edge 24 that is defined by the distal tips of the teeth. The dermal punch 20 can be a pair of walls 26, such as seen in FIG. 4B. The walls 26 have an external convex surface that are connected to each other at a pair of mating edges 28. Referring back to FIG. 4A, a longitudinal axis 50 is defined by the interface of the cutting edge 22 with the mating edges 28. A vertical axis 52 intersects the longitudinal axis 50 and is interposed between the mating edges 28.

While the above refers to a pair of walls with a pair of mating edges, it is recognized that the walls can be formed by several methods including welding of two convex pieces or drawing an integral tube to the desired shape.

In this embodiment, the projecting edge 24 has a convex shape with a portion that extends the furthest distally, being spaced equidistant from the mating edges 28 and located the furthest from the longitudinal axis 50. This point on each wall 26 is defined as an apex 54.

Figure 5:
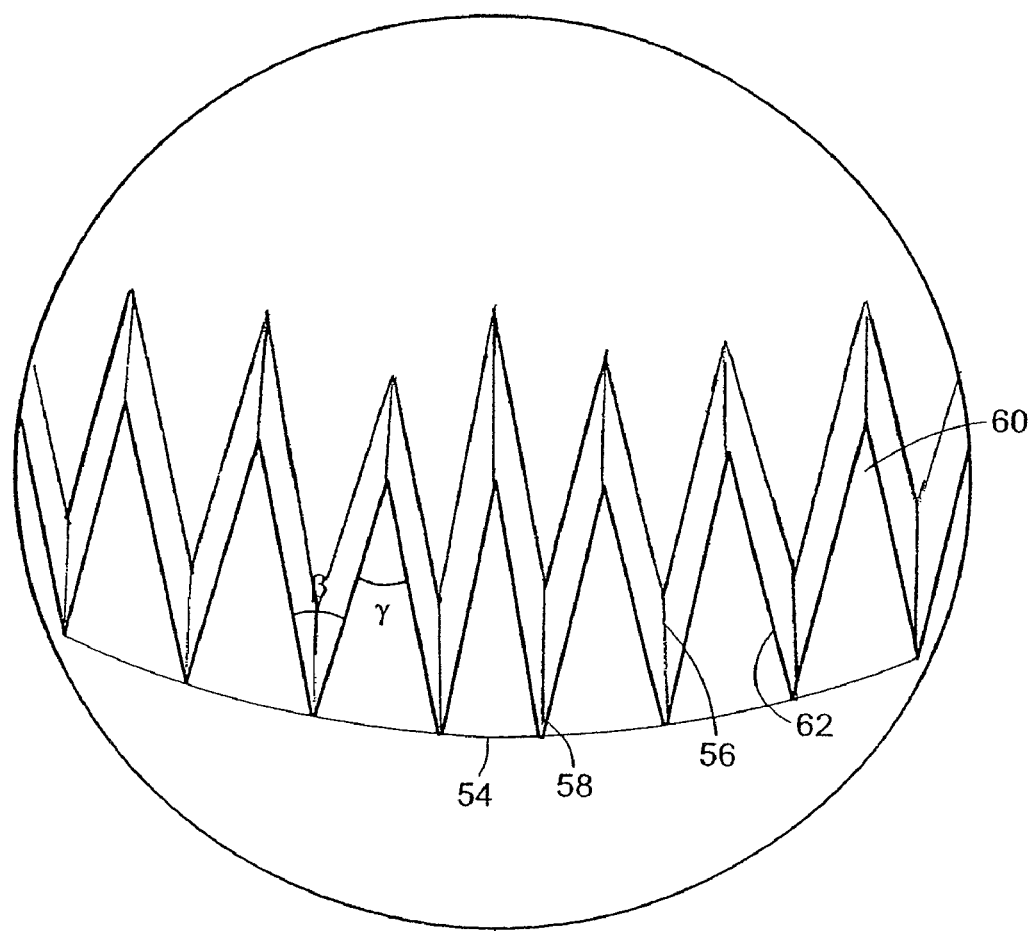
FIG. 5 is an enlarged view of a plurality of saw teeth of the dermal punch taken along 5 of FIG. 4A.

The dermal punch 20 has a sawtooth or serrated edge 56 wherein each tooth 56 has a tip 58 positioned on the projection edge 24 and a root 60 interposed between each tooth 56 as best seen in FIG. 5. The sawtooth 56 has a knife edge 62 on the tooth surface 62 for cutting. The knife edge 62 on the tooth surface increases the cutting length, which is the length on the dermal punch that is capable of cutting the skin.

In a preferred embodiment, the knife edge has one surface shaped similar to a number 11 scalpel blade. The sawtooth shape with a knife edge extends between adjacent tips 58 and roots 60 therein allowing for an increased cutting length. In a preferred embodiment, the cutting length is greater than twice the length of the projecting edge 24. It is recognized that the projecting edge is a projection and not a physical edge and extends from tip to tip of the saw teeth. In one preferred embodiment, the cutting length is in a range of 2 to 4 times the length of the projection edge.

In addition, the cutting edge 22 of the dermal punch 20 is formed by the pair of walls that have an external convex surface and engage each other at the mating edges 28 as seen in FIG. 4B. The two walls 26 each contain the convex shaped projection edge 24 with the sawtooth shape. These two convex walls 26 define an angle at the mating edges.

Referring to FIG. 5, an enlarged side view of eight sawteeth of the cutting edge 22 of the dermal punch 20 in accordance with a preferred embodiment of the invention, is shown. The cutting edge 22 of the sawtooth has each tip located along the projecting edge 24. Each tooth is oriented such that a vertical axis extending from the tip of the tooth extends through the base of the tooth, and preferably at the center or in proximity to the center of the base. The bevel of the cutting edge is shown in FIG. 5.

In a preferred embodiment, the dermal punch 20 has 12 to 18 teeth per wall 26. Each tooth has a tip angle of $\beta$ that in one embodiment is in a range of 15° to 35° and in a preferred embodiment is in a range of 22° to 28°. In addition, the root angle is $\gamma$ and is in a range of 15° to 35° and in a preferred embodiment is in a range of 22° to 28°. Each of the two surfaces has a knife or cutting edge 62 as indicated above. In an embodiment, the knife edge 60 is shaped like a number 11 scalpel blade. In one embodiment, the knife edge is like a number 11 scalpel blade, with the knife edge, looking in cross section of the wall, extending from one surface to the other surface. In another embodiment, a pair of knife edge looking in cross section of the wall, each extend from the center line to another surface.

Figure 6A:
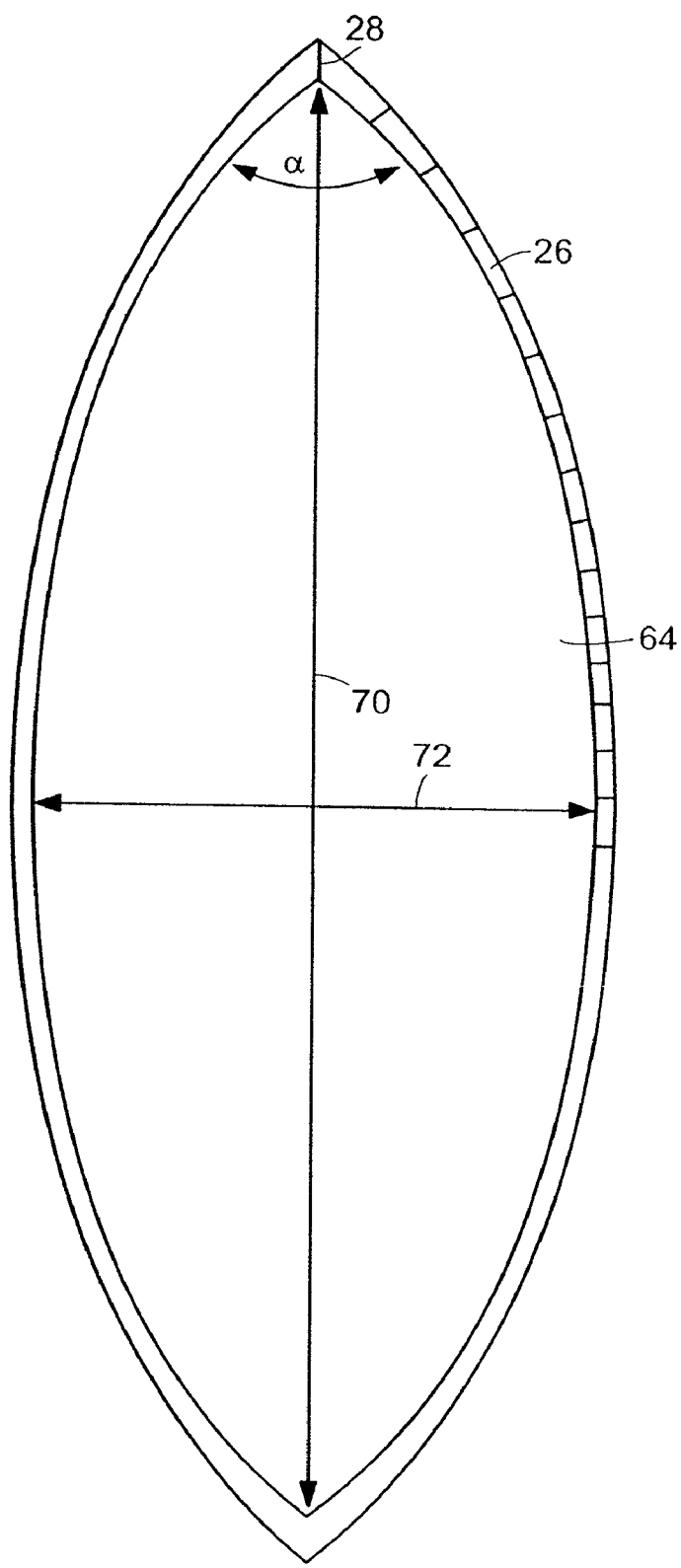
FIG. 6A is a bottom view of the dermal punch in accordance with a preferred embodiment of the present invention.

Referring to FIG. 6A, a bottom enlarged view of the dermal punch 20 is shown in accordance with a preferred embodiment of the present invention. The two walls 26 are connected to each other at the mating edges 28. The two walls 26 define an angle $\alpha$ at the edges 28. The angle $\alpha$ in a preferred embodiment is between 75° and 115°, and in the example discussed herein is 90°. The ratio of the major axis 70 to that of the minor axis 72 is preferably between a range of 3 to 1 and 4 to 1. In one preferred embodiment, the major axis 70 has a length of 6 millimeters and the minor axis 72 is 2 millimeters. Therefore, the ratio of major axis to minor axis is 3 to 1. In the illustrated embodiment, the overall depth from the apex 54 to the longitudinal axis 50, the location of the highest root 60, is 2 millimeters. The greatest distance between the tip 58 and the adjacent root 60 of the teeth 56 is 1 millimeter. The opening 64 between the pair of walls 26 receives the sample tissue.

The walls 26 define an opening 64 that has a fusiform or spindle shape. A major axis 70 of the opening 64 extends from one mating edge 28 to the other mating edge 28. A minor axis 72 extends from one wall 26 to the other wall 26 perpendicular to the major axis 70.

It is recognized that in certain embodiments that the distance between the tip 58 and the adjacent root 60 is greater than 1 millimeter, such as 1.5 millimeters in an embodiment for thick skin of the back or for "excision" of larger lesions mitigating the need for a scalpel excision.

Figure 6B:
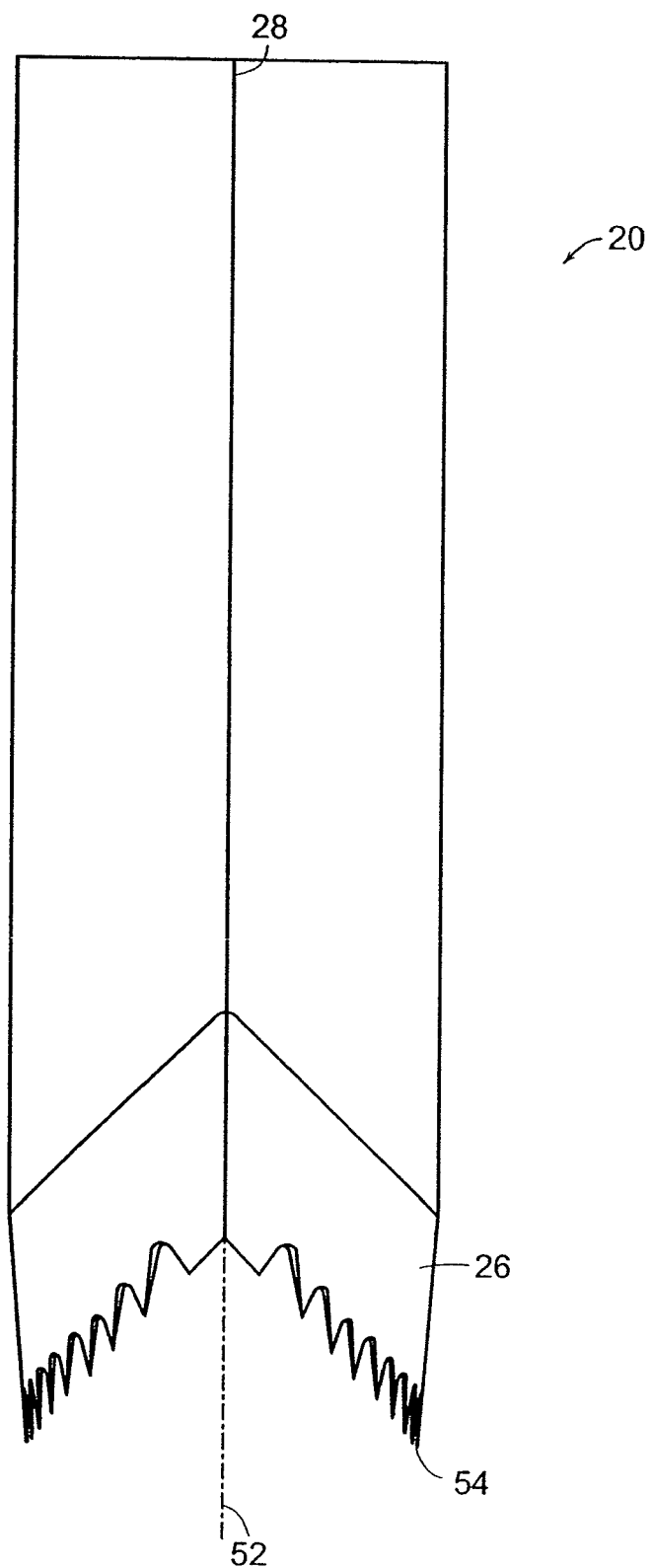
FIG. 6B is a side view of the dermal punch in accordance with a preferred embodiment of the present invention.

FIG. 6B is a side view of the dermal punch 20 of a preferred embodiment of the invention. The mating edge 28 between the two walls 26 extends vertically. The two walls 26 each have a convex shape projecting outward from the mating edge 28 to the point where the apex 54 from the projection edge is furthest from the longitudinal axis 50 which projects in and out of the paper in FIG. 6B. FIG. 6B shows the walls in proximity to the cutting surfaces tapering towards each other. It is recognized that the walls can be parallel to each other in certain embodiments.

The dermal punch 20 is positioned next to the skin so that the apex 54 of each of the walls is positioned so that the skin to be tested is positioned between the walls. The dermal punch 20 is pushed into the skin with a vertical and slightly rocking motion until the roots of all of the teeth have entered the skin (i.e. until the longitudinal axis 50 is in the same plane as the surface of the skin.)

The tips of the teeth engage and puncture the skin. As the dermal punch 20 is pushed into the skin, the cutting edge slices the skin (tissue) in a region of interest. The teeth provide a longer cutting surface and require less pressure to excise the sample. Therein, the dermal punch 20 is capable of producing a tissue sample with side walls or edges that are near perpendicular to the upper surface of the skin. The angle of sidewalls can vary slightly from a perpendicular orientation to facilitate bringing the skin edges together when closing the biopsy site. In that the dermal punch does not need to be rotated to cut the tissue sample, the fusiform-spindle-shape can be used.

Figure 7A:
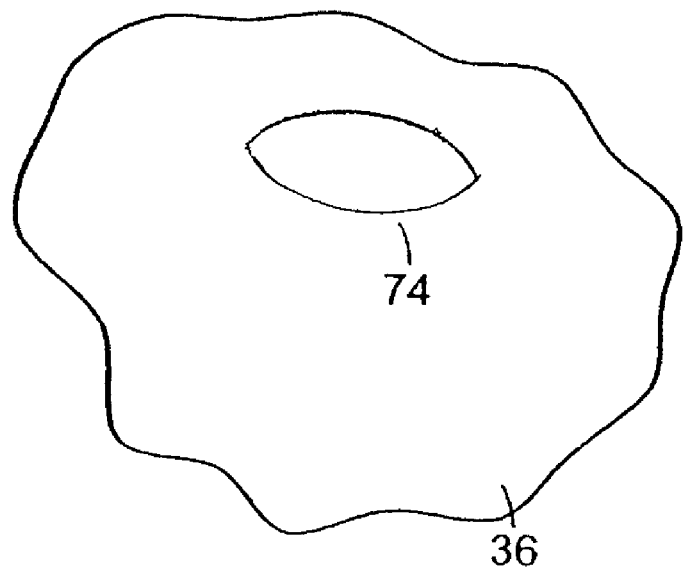
FIG. 7A is a view of an example of the wound caused by the dermal punch in accordance with a preferred embodiment of the present invention.
Figure 7B:
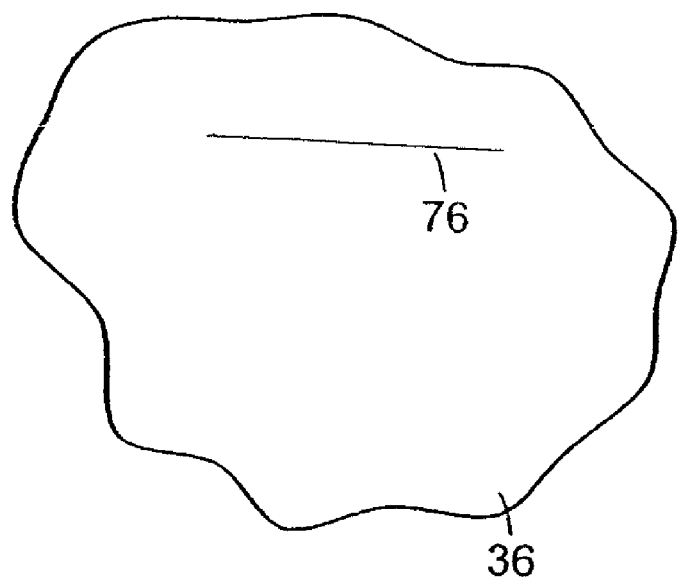
FIG. 7B is a view of the example of the "final scar" from the wound of the dermal punch.

The resulting wound from the dermal punch 20 has a smooth shape similar to the shape of a dermal punch as seen in FIG. 7A. Therefore, the resulting closed wound forms a line as seen in FIG. 7B as compared to the dog ear illustrated in FIG. 2C, resulting from the wound mark as seen in FIG. 2A. In addition, the sample that is to be removed from the skin, such as a skin growth, or a mole, or portion thereof, typically does not have a circular shape. The long axis or major axis 70 of the opening 64 of the dermal punch 20 can be oriented with respect to the largest dimension of the mole or tissue sample to be removed.

Figure 8:
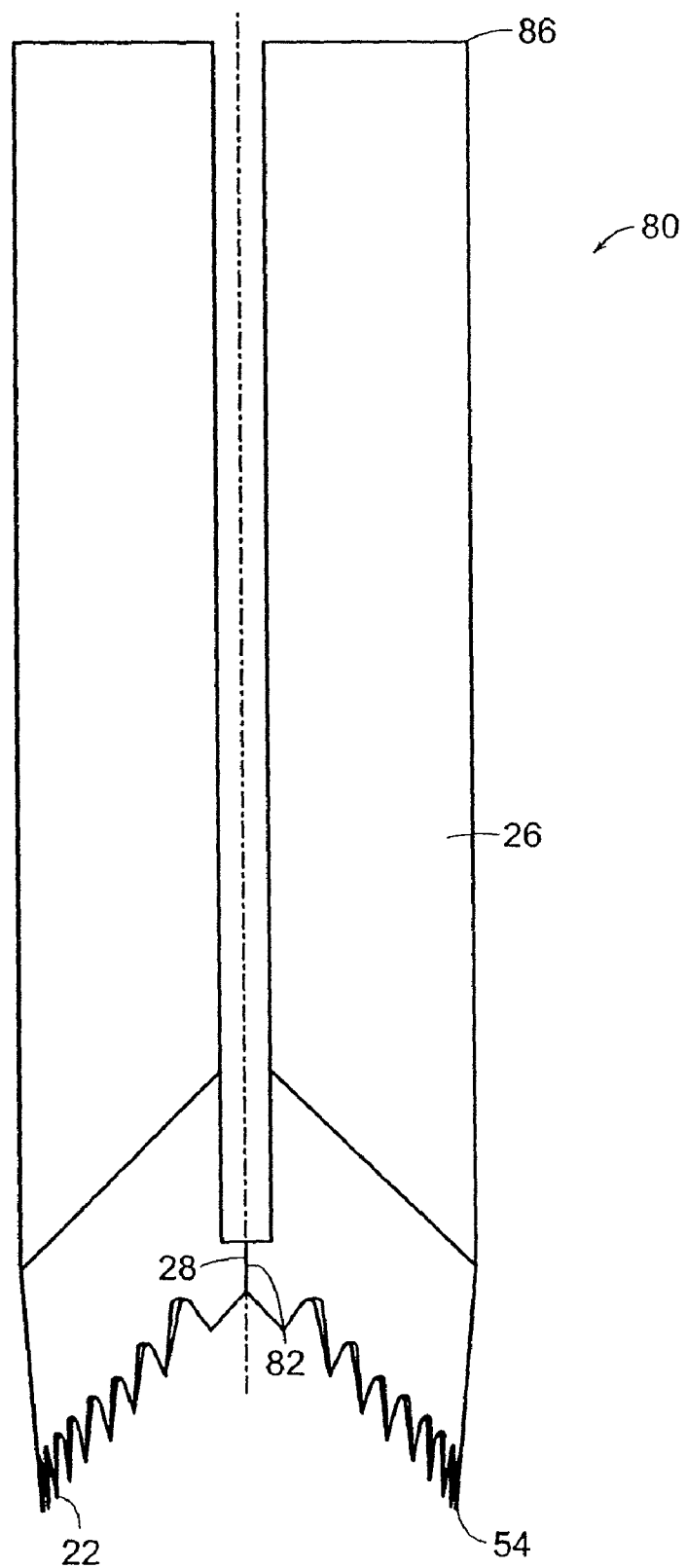
FIG. 8 is a side view of an alternative embodiment of a dermal punch.

FIG. 8 illustrates an alternative embodiment dermal punch 80 in accordance with the invention. The dermal punch 80 has a pair of walls 26 that are connected at a single point 82 on a mating edge 28. The single point, a movable hinge 82, allows the two pairs of walls 26 to move relative to each other. Therefore, the pair of walls 26 with the cutting edge 22 are pushed into the skin to cut the skin generally in the shape of the opening 64 formed by the convex shape of the two walls 26. In most cases the tissue that has been cut will adhere to the dermal punch where one side of the blade works to "hook" the tissue for removal from the body. Occasionally the sample will remain adhered to the body through the underlying fat layer. In order to facilitate the removal of the skin sample 38, the upper edge 86 of the walls 26 of the dermal punch 80 are moved apart from each other therein allowing the blade or cutting edges 22 to move closer together. Even the slightest movement of the apexes 54 of the walls 76 changes the shape of the opening 64 relative to the skin sample 38 causing the grabbing and retention of the skin sample 38. Relaxation of the side walls allows the sample to be easily deposited in a specimen cup.

Figure 9:
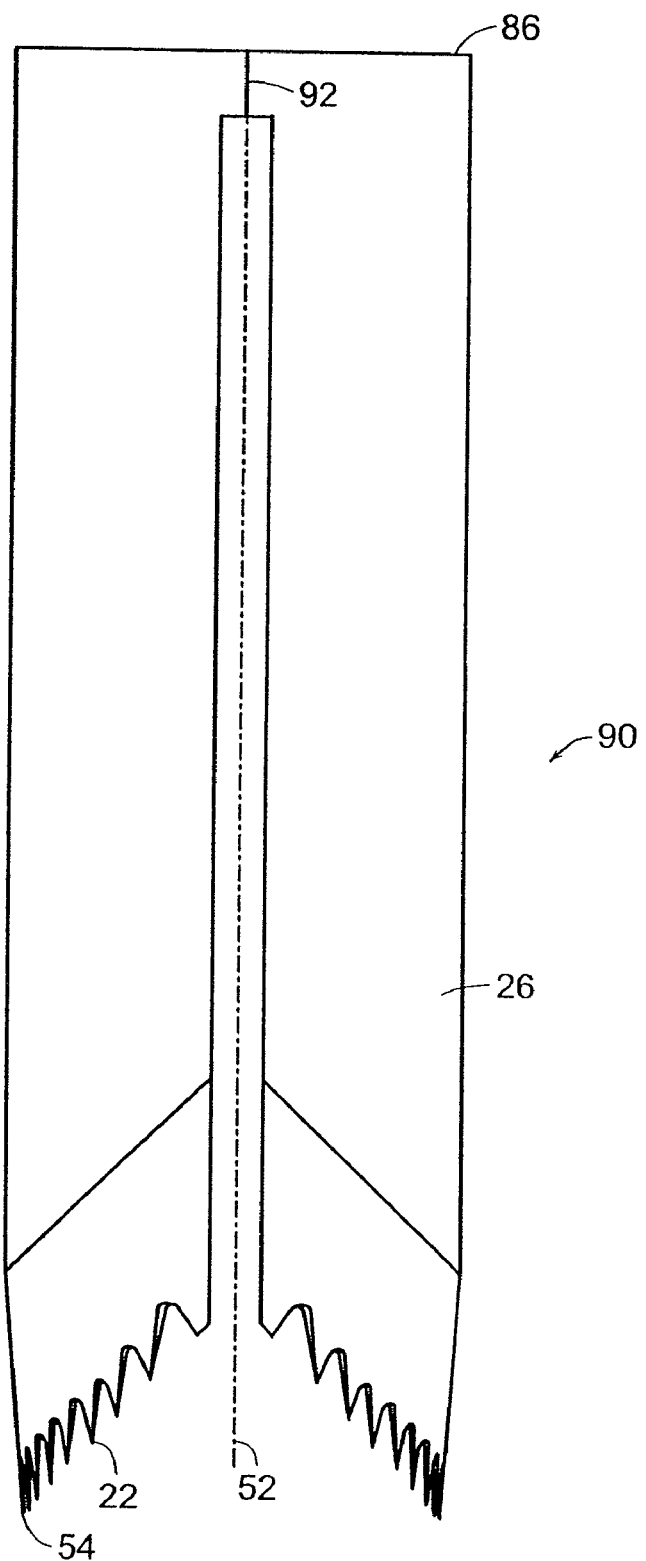
FIG. 9 is a side view of another alternative embodiment of a dermal punch.

In the alternative, a dermal punch 90 is formed such that a pair of walls 26 are formed in a similar shape to that discussed above, however, the walls 26 are joined at a point 92 only at the mating edge 28 at the upper edge 86, i.e., the edge furthest from the cutting or blade edge 22, as seen in FIG. 9. After being inserted into the body to excise the tissue or skin sample 38 from the remaining skin, the walls 26 of the dermal punch 90 are squeezed below the point 92 to move the free edges, i.e., the cutting edges 22 of each wall towards each other to reduce the space between the pair of walls 26.

Figure 10A:
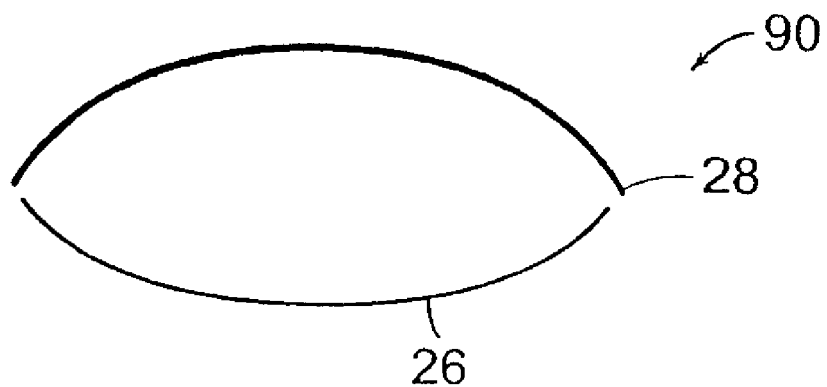
FIG. 10A is a bottom view of the dermal punch in an insert position in accordance with a preferred embodiment of the present invention.
Figure 10B:
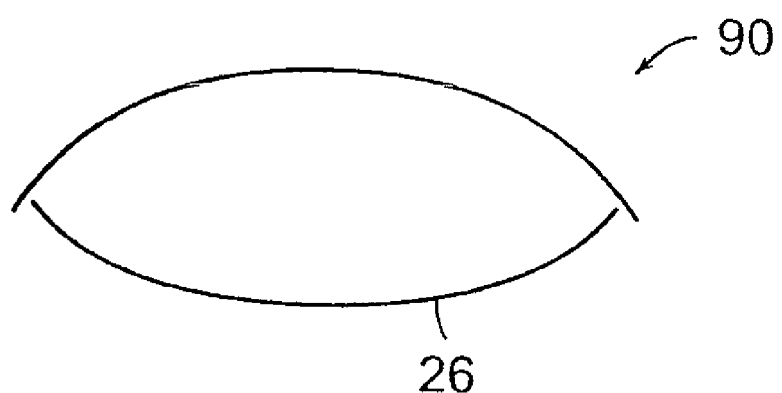
FIG. 10B is a bottom view of the dermal punch in a retract position in accordance with a preferred embodiment of the present invention.

FIG. 10A shows the pair of walls 26 at a position when the dermal punch 90 is inserted into the skin to create the straight vertical cuts. FIG. 10B shows the relative position of the walls 26 when the walls are moved together to allow removal of the skin patch 38.

Figure 11:
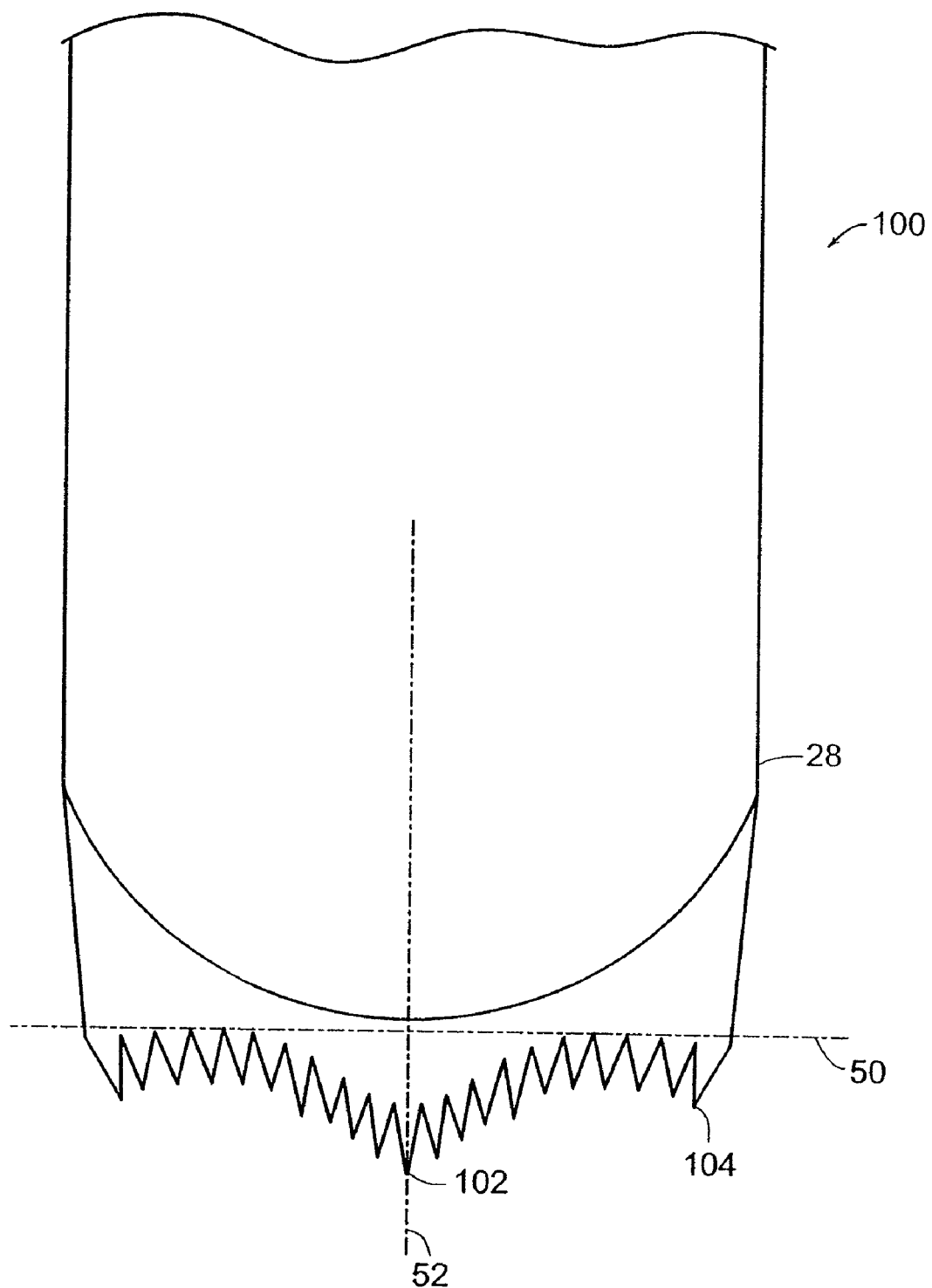
FIG. 11 is a front view of an alternative embodiment of a dermal punch.

Referring back to FIG. 4A, the saw teeth or serrated edges 56 are shown with the tip extending further down as they are further away from the mating edge 28, wherein the apex, equally spaced from the mating edges 28, is the farthest projection from the longitudinal axis 50. In contrast, FIG. 11 shows an alternative embodiment wherein the point 102, i.e., tip, that projects the furthest from the longitudinal axis 50, similar to FIG. 4A is a point being equally distant from the mating edges 28. However, the second furthest projecting point 104 from the longitudinal axis 50 is in proximity to the mating edge 28.

When the dermal punch 100 of FIG. 11 is placed into contact with the skin, the point 102 on each of the walls 26 that are equally distant from the mating edge 28 touch and puncture the skin first. This is similar to the embodiment shown in FIG. 4A. In contrast, the next points 104 are each in proximity to the mating edges 28. Therefore instead of cutting in two directions away from each apex, the skin is initially cut at four separate and distinct positions i.e., the apexes and the mating edges 28 and the cuts move towards each other as the dermal punch 100 is inserted. The cutting from the "four corners" retains the tissue in position as it is cut.

In a preferred embodiment, the distance between the apex and the longitudinal axis, the location of the highest root, is 1 millimeter. The vertical position of the tips do not vary as greatly as the embodiment shown in FIGS. 3-5.

Figure 12:
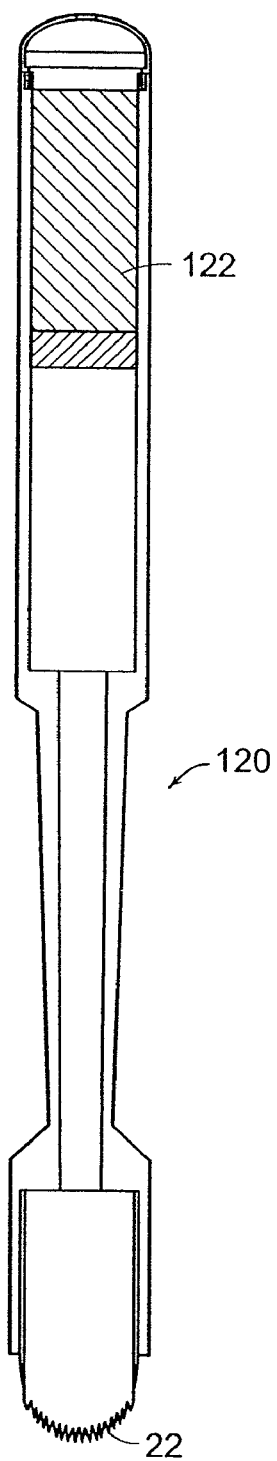
FIG. 12 is a side sectional view of a dermal punch with a glue dispenser in accordance with a preferred embodiment of the present invention.

After the skin sample 38 from the area of interest is removed from the body, the wound may be closed using traditional "stitching." Alternatively, FIG. 12 shows an alternative embodiment of a dermal punch 120. The dermal punch 120 has the cutting edges 22 at one end and a medical glue or adhesive dispenser 122 located at the other end so that the surgeon can simply turn the tool around to apply a medical adhesive such as DERMABOND® marketed by Ethicon, Inc. The medical adhesive dispenser 122 can be used with other embodiments of the dermal punch. The distal end of the walls 26 of the dermal punch 120 are compressed to allow a flow of the medical adhesive to be applied to the wound in thin layers.

Figure 13:
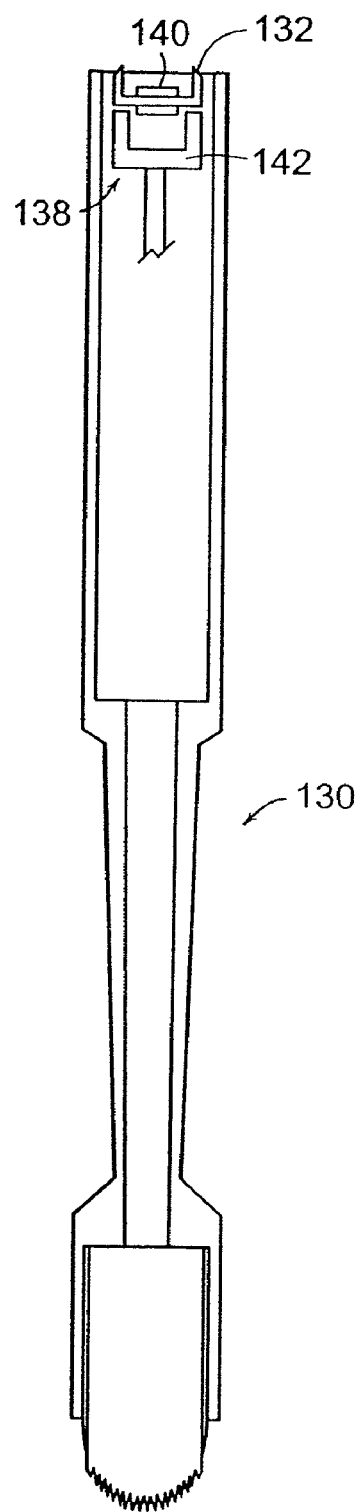
FIG. 13 is a side sectional view of a dermal punch with a skin stapler in accordance with a preferred embodiment of the present invention.

An alternative method of closing the wound is to staple or "clip" the wound. FIG. 13 shows an alternative embodiment of a dermal punch 130. The dermal punch 130 has a mechanism 138 that retains at least one staple or clip 132 and is located at one end of the dermal punch 130 opposite to that of the cutting edge 22. The mechanism 138 has a retainer 140 for holding the staple 132 and a crimping bar 142. The crimping bar 142 slides to bend the staple 132 and interacts with the retainer 140 to release the staple 32. Whether closed by stitching, adhesive, staple, or tape, the dermal punch according to the invention reduces or eliminates scar depression.

Figure 14A:
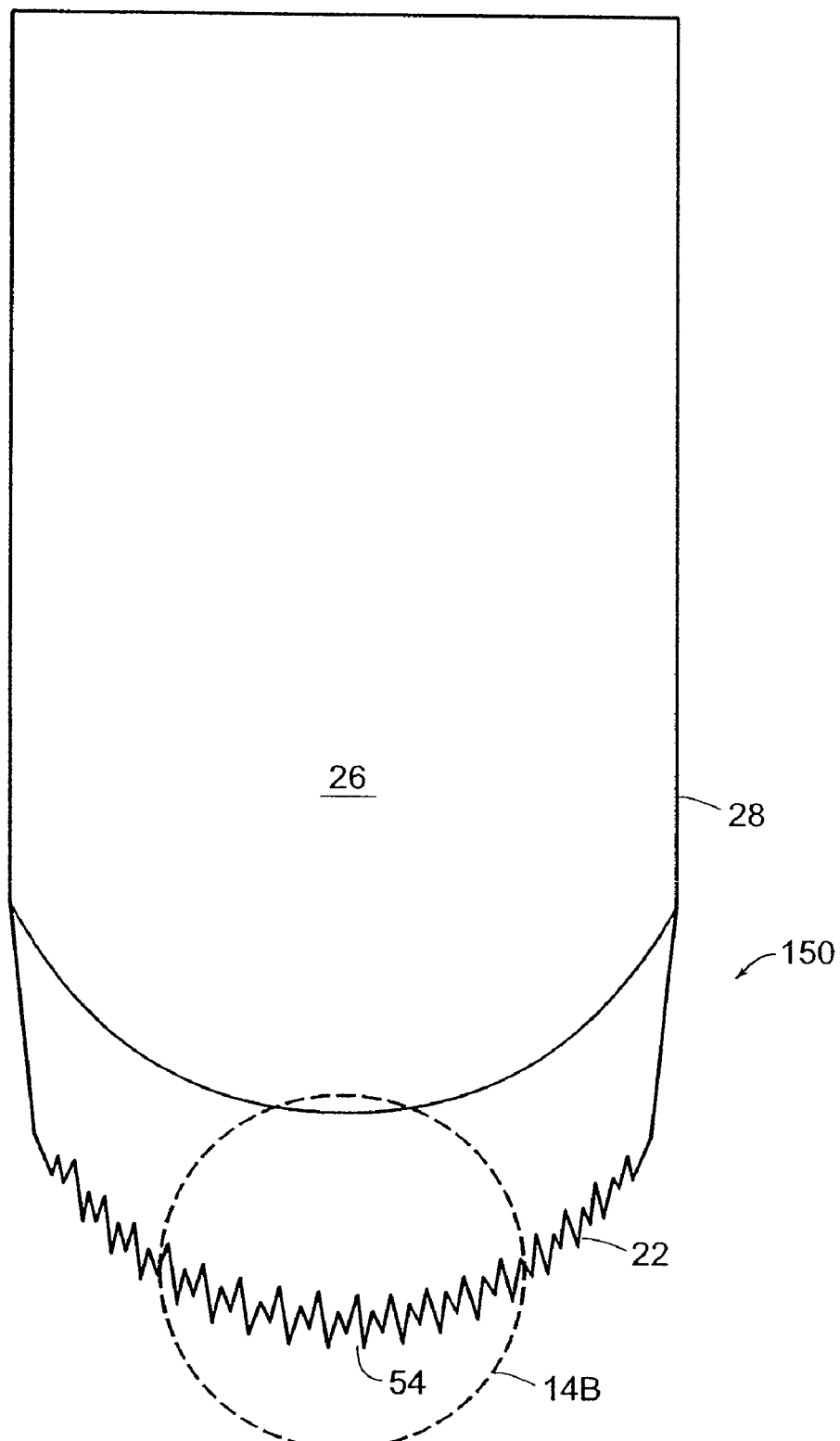
FIG. 14A is an enlarged side view of an alternative embodiment of a dermal punch.
Figure 14B:
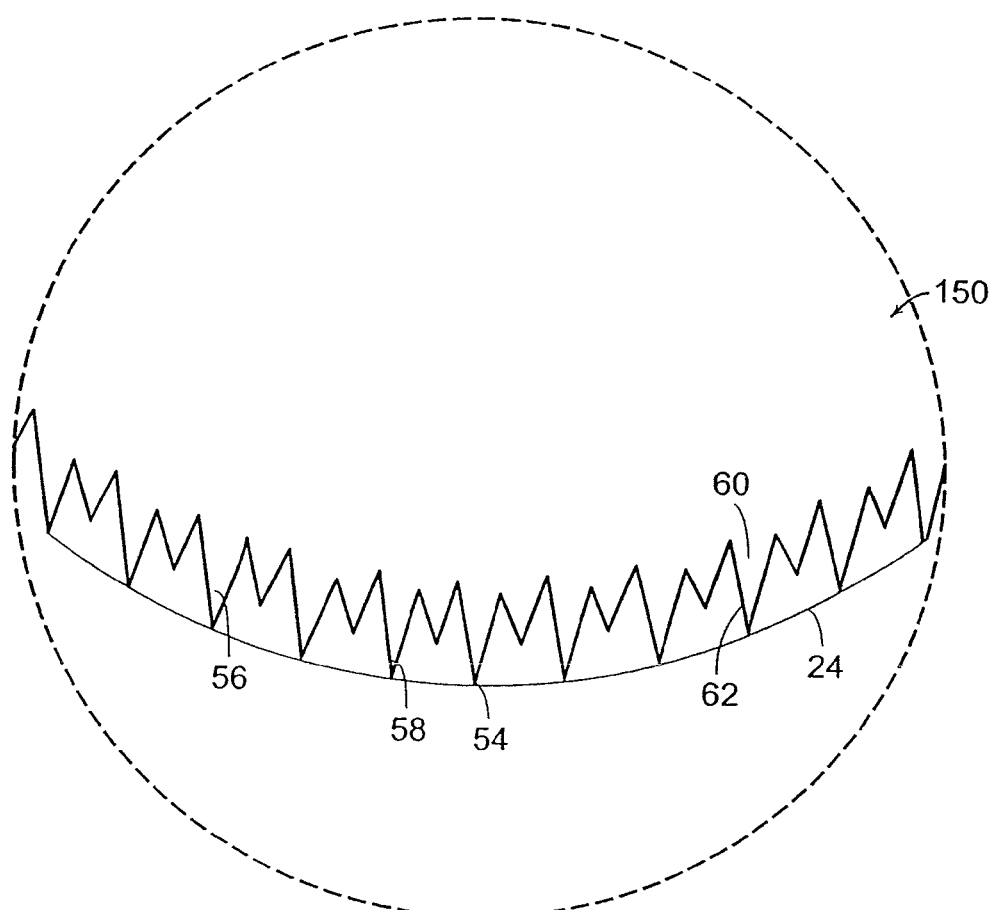
FIG. 14B is an enlarged side view of a plurality of saw teeth of the dermal punch taken along 14B of FIG. 14A.

An alternative embodiment of a dermal punch 150 is shown in FIGS. 14A and 14B. The dermal punch has a sawtooth or serrated edge similar to that shown in FIGS. 5A and 5B, but in addition has a set of secondary sawtooth edges that are shorter and interposed between the longer teeth.

It is recognized that the dermal punch can have all the tips equally distant from the longitudinal axis, the longitudinal axis being defined as the location of the highest root. It is also recognized that the dermal punch can have all the roots of the teeth located on the longitudinal axis.

In accordance with a preferred embodiment, the dermal punch or a portion thereof is disposable and is formed of plastic and has a stainless steel cutting edge. It is recognized that the dermal punch can be formed of materials such as, for example, stainless steel or plastic, that are bio-compatible, can hold an edge and cut sharply.

Preferred embodiments of the present invention can include a kit having dermal punches of selected sizes and removal areas to accommodate the different sizes and shapes of lesions. The kit can include a single handle with a plurality of distal punch elements that can be mounted and detached as needed or a plurality of dermal punches of different sizes that are each packaged in separate sterilized packages for single use.

It is recognized that the dermal punch can, in an embodiment, have the convex walls with a smooth cutting edge without sawteeth or serrated edge.

The claims should not be read as limited to the described order or elements unless stated to that effect. Therefore, all embodiments that come within the scope and spirit of the following claims and equivalents thereto are claimed as the invention.

What is claimed is:

1. A method of collecting tissue from a region of skin comprising the steps of:
   holding a dermal punch having a cutting edge extending along a first wall with a first plurality of teeth and a second wall with a second plurality of teeth, the first wall and second wall meeting at mating edges to define a cavity having a fusiform shape, the cavity having a major axis and a minor axis that are perpendicular to a vertical axis of the dermal punch, each of the teeth extending in a distal direction that is parallel to the vertical axis of the dermal punch, at least one first apex tooth projecting at an apex of the first wall and at least one second apex tooth projecting at an apex of the second wall to define a plurality of apex teeth and at least one mating edge tooth projecting at each mating edge at which the first wall meets the second wall to define a plurality of edge teeth, the plurality of apex teeth and the plurality of edge teeth defining four corners of the cutting edge;
   positioning the cutting edge relative to a selected region of skin of a patient;
   initially puncturing the skin at all four corners of the cutting edge with the apex teeth and the mating edge teeth of the dermal punch by pushing the teeth along the vertical axis that is perpendicular relative to the region of skin; and
   continuing to insert additional portions of the cutting edge into the skin of the patient to cut the selected region of skin.

2. The method of claim 1 wherein the step of positioning includes placing the apex teeth and the mating edge teeth of the cutting edge in contact with the skin with the selected region of skin interposed between the first wall and the second wall such that a cut region moves toward an adjacent cut region during insertion of the cutting edge into the skin.

3. The method of claim 1 further comprising the step of removing the selected region of skin from a body by moving the dermal punch in a motion perpendicular to the skin.

4. The method of claim 1 further comprising the step of closing a wound on the skin, the wound resulting from removal of the selected region of skin from the patient.

5. The method of claim 4 further comprising closing the wound in the skin with an adhesive.

6. The method of claim 4 further comprising closing the wound in the skin with a surgical staple.

7. The method of claim 1 further comprising holding a handle of the dermal punch, the first wall and the second wall meeting at edges at an angle α, the first wall and the second wall being moveable.

8. The method of claim 7 further comprising using a dermal punch in which the angle α is between 75° and 115°.

9. The method of claim 1 further comprising using the dermal punch wherein a maximum distance from one of the apex teeth to the major axis is 2 mm.

10. The method of claim 1 further comprising tilting the dermal punch in a lateral direction to remove a tissue sample in the cavity.

11. A dermal punch comprising:
    a handle having a vertical axis; and
    a blade attached to the handle and having a first convex wall with a first plurality of teeth and a second convex wall with a second plurality of teeth, the first wall and the second wall forming a fusiform shaped cavity having a major axis and a minor axis shorter than the major axis such that the first plurality of teeth and the second plurality of teeth define a four corner cutting edge, each of the plurality of teeth extending in a distal direction that is parallel to the vertical axis;
    the four corner cutting edge including the first wall having a first apex tooth and a first edge tooth and the second wall having a second apex tooth and a second edge tooth such that cuts move toward each other between an apex tooth and an adjacent edge tooth along the cutting edge during insertion into a region of skin of a patient.

12. The dermal punch of claim 11 wherein the teeth have tips and roots, a maximum distance between a tip and adjacent root being 1 mm.

13. The dermal punch of claim 11 wherein the first wall has at least 12 teeth and the second wall has at least 12 teeth.

14. The dermal punch of claim 12 wherein the plurality of teeth define a cutting length that is in a range of 2 to 4 times a length of a projecting edge of the teeth.

15. The dermal punch of claim 14 wherein the cutting length is greater than twice the length of the projecting edge.

16. The dermal punch of claim 11 wherein a distance between a tip and a root of each tooth is at least 1 mm.

17. The dermal punch of claim 16 wherein the tip of the teeth in proximity to the mating edge of the first wall extends in a distal direction approximately a length of a tooth apex.

18. The dermal punch of claim 11 wherein the first wall and the second wall are connected to each other at a pair of movable mating edges, and a ratio of the minor axis to the major axis is between 1 to 3 and 1 to 4.

19. The dermal punch of claim 11 to further comprising a device for applying medical glue.

20. The dermal punch of claim 11 further comprising a device for applying at least one staple to an incision in the region of skin of a patient.

21. The dermal punch of claim 11 wherein the teeth have a sawtooth shape and each of the plurality of teeth has a root angle of between 15° and 35° and a tip angle between 15° and 35°, the tooth having a minimum length of 2 millimeters.

22. The dermal punch of claim 11 wherein a portion of the cutting edge for each wall has a concave region.

23. The dermal punch of claim 11 further comprising a mechanism for closing the wound.

24. The dermal punch of claim 11 further comprising a kit including a plurality of blades having different sizes.

25. The dermal punch of claim 11 wherein the blade is removable from the handle.

26. The dermal punch of claim 11 wherein each edge tooth projects further distally relative to an adjacent portion of the cutting edge.

* * * * *